United States Patent [19]

Hechenbleikner

[11] 4,064,100
[45] Dec. 20, 1977

[54] FRIABLE DISTEARYL PENTAERYTHRITOL DIPHOSPHITE

[75] Inventor: Ingenuin Hechenbleikner, West Cornwall, Conn.

[73] Assignee: Weston Chemical Co., Inc., Montvale, N.J.

[21] Appl. No.: 697,637

[22] Filed: June 18, 1976

Related U.S. Application Data

[63] Continuation of Ser. No. 598,166, July 22, 1975, abandoned, which is a continuation of Ser. No. 203,034, Nov. 29, 1971, abandoned.

[51] Int. Cl.$^2$ .......................... C07F 9/09; C08K 5/32
[52] U.S. Cl. .......................... 260/45.8 R; 260/45.95F; 260/927 R; 260/982

[58] Field of Search ............ 260/982, 927 R, 45.95 F, 260/45.8 R, 45.7 PH

[56] References Cited

U.S. PATENT DOCUMENTS

| | | | |
|---|---|---|---|
| 2,961,454 | 11/1960 | Gould et al. | 260/982 X |
| 3,047,608 | 7/1962 | Friedman et al. | 260/927 R X |
| 3,205,250 | 9/1965 | Hechenbleikner | 260/982X |
| 3,988,293 | 10/1976 | Mills | 260/45.8 R |
| 4,000,101 | 12/1976 | McNally | 260/45.8 R X |

Primary Examiner—Richard L. Raymond
Attorney, Agent, or Firm—Cushman, Darby & Cushman

[57] ABSTRACT

Free flowing distearyl pentaerythritol diphosphite is prepared. The product is non-toxic.

23 Claims, No Drawings

FRIABLE DISTEARYL PENTAERYTHRITOL DIPHOSPHITE

This is a continuation of application Ser. No. 598,166 filed July 22, 1975, and now abandoned, which application is a continuation of application 203,034 filed Nov. 29, 1971, and now abandoned.

Distearyl pentaerythritol diphosphite has been prepared in the past as a waxy, non-friable solid. It contained some triphenyl phosphite and other phenoxy groups. Because of the presence of phenolic material in the product, it has encountered food and drug problems. Also its waxy nature renders it difficult to handle and to blend in polymeric systems. Typical methods of preparing such a waxy distearyl pentaerythritol diphosphite are disclosed, for example, in Gould U.S. Pat. No. 2,961,454, Friedman U.S. Pat. No. 3,047,608, and Hechenbleikner U.S. Pat. No. 3,205,250.

It has now been found that distearyl pentaerythritol diphosphite can be prepared as a non-waxy friable, colorless, hard, dry solid with a very low odor, having a solidification point of 55°-60° C. It can be readily ground to a free flowing, non-caking white powder, e.g. of 200 mesh size or less.

The distearyl pentaerythritol diphosphite of the present invention is prepared by reacting diphenyl pentaerythritol diphosphite with stearyl alcohol in an excess of at least 10% molar excess. The excess stearyl alcohol can be 50% or even 100% on a molar basis. The distearyl pentaerythritol diphosphite can also be prepared by reacting pentaerythritol, triphenyl phosphite and stearyl alcohol, using the same amount of excess stearyl alcohol. There can be used any conventional phosphite esterification catalyst, preferably an alkaline catalyst such as sodium methylate, sodium decylate, sodium octadecylate, potassium methylate, metallic sodium, sodium hydrate, sodium phenolate, etc. The catalyst can be employed in conventional amounts, e.g. 0.1–5% by weight.

The product prepared in the present invention consists of 85–90% distearyl pentaerythritol diphosphite, 5–10% stearyl alcohol and traces of tripentaerythritol tetraphosphite and tristearyl phosphite as incidental impurities.

The distearyl pentaerythritol diphosphite composition of the present invention is useful wherever the known distearyl pentaerythritol diphosphite is used and has the advantages of being able to be ground to a free flowing powder, being free of phenolic odor and especially having advantages due to its extremely low toxicity for food and drug application. In chick embryo tests the distearyl pentaerythritol diphosphite of the invention exhibits no toxicity. Also, there was no $LD_{50}$ at 10 grams/kilogram of body weight in tests on rats.

The distearyl pentaerythritol diphosphite composition of the present invention prevents processing degradation of olefin and vinyl halide polymers in the melt and exhibits synergistic stability with ultraviolet light stabilizers, e.g. benzophenones such as 2-hydroxy-4-methoxy-benzophenone, 2, $2^1$-dihydroxy-4-methoxy benzophenone, 2, $2^1$-dihydroxy-4-n-octoxy benzophenone, and 2-hydroxy 4-n-octoxy benzophenone, benzotriazoles, e.g. 2($2^1$-hydroxy-$5^1$-methyl phenol) benzotriazoles, etc.

Previously excess stearyl alcohol was not employed in preparing distearyl pentaerythritol diphosphite, possibly because it was believed that the use of excess stearyl alcohol would cause the formation of polymers and other types of stearyl pentaerythritol phosphites.

When the distearyl pentaerythritol diphosphite compositions of the invention are used to stabilize polymers, they are used in an amount of 0.005 to 10 parts per 100 parts of polymer. Usually they are used in olefin polymers in an amount of 0.05–1%, preferably 0.1–0.5%, and with vinyl halide polymers in an amount of 0.2–1.0%.

The distearyl pentaerythritol diphosphite compositions can be used as heat and light stabilizers for resins made from vinylidene compounds such as vinyl chloride, vinylidene chloride, vinyl chloroacetate, chlorostyrenes, vinyl bromide and chlorobutadienes.

Such vinylidene compounds may be polymerized alone or in admixture with each other or with vinylidene compounds free from halogen. Among the halogen free materials which can be copolymerized with the halogen containing vinylidene compounds, e.g. vinyl chloride, are vinyl esters of carboxylic acids, e.g. vinyl acetate, vinyl propionate, vinyl butyrate and vinyl benzoate, esters of unsaturated acids, e.g. alkyl and alkenyl acrylates such as methyl acrylate, ethyl acrylate, propyl acrylate, butyl acrylate and allyl acrylate as well as the corresponding methacrylates, e.g. methyl methacrylate and butyl methacrylate, vinyl aromatic compounds, e.g. styrene, p-ethyl styrene, divinyl benzene, vinyl naphthalene, x-methyl styrene, p-methyl styrene, dienes such as butadiene and isoprene, unsaturated amides such as acrylamide, methacrylamide and acrylanilide and the esters of α, β-unsaturated carboxylic acids, e.g. the methyl, ethyl, propyl, butyl, amyl, hexyl, heptyl, octyl, allyl, methallyl and phenyl esters of maleic, crotonic, itaconic and fumaric acids and the like. Specific examples of such esters are diethyl maleate, dibutyl maleate and dibutyl fumarate.

The copolymers in which at least 50% of the copolymer is made from a halogen containing vinylidene compound such as vinyl chloride are preferably treated according to the invention.

The stabilizers of the present invention are also effective when intimately mixed with halogen containing resin in which part or all of the halogen is introduced into a preformed resin, e.g. chlorinated polyvinyl acetate, chlorinated polystyrene, chlorinated polyethylene, chlorinated polyvinyl chloride, chlorinated natural and synthetic rubbers and rubber hydrochloride.

Typical examples of copolymers include vinyl, chloridevinyl acetate (95:5 weight ratio), vinyl chloride-vinyl acetate (87:13 weight ratio), vinyl chloride-vinyl acetate-maleic anhydride (86:13:1 weight ratio), vinyl chloride-vinylidene chloride (95:5 weight ratio), vinyl chloride-diethyl fumarate (95:5 weight ratio), vinyl chloride-trichloroethylene (95:5 weight ratio).

The resin, e.g. polyvinyl chloride, can either be plasticized or unplasticized. As the plasticizer there can be employed conventional materials such as dioctyl phthalate, octyl decyl phthalate, tricresyl phosphate, 2-ethylhexyl diphenyl phosphate, dodecyl dicresyl phosphate, tributyl acetyl citrate, dioctyl sebacate, dibutyl sebacate, etc. The plasticizer is used in conventional amount, e.g. 10 to 100 parts for each 100 parts of the vinyl chloride containing resin.

There can also be incorporated 0.1 to 10 parts per 100 parts of the halogen containing resin of a metal salt stabilizer. Thus, there can be used barium, strontium, calcium, cadmium, zinc, lead, tin, magnesium, cobalt, nickel, titanium and aluminum salts of phenols, aromatic carboxylic acids, fatty acids and epoxy fatty acids.

Examples of suitable salts include barium di(nonylphenolate), strontium di(nonylphenolate), strontium di(amylphenolate), barium di(octylphenolate), strontium di(octylphenolate), barium di(nonyl-o-cresolate), lead di(octylphenolate), cadmium-2-ethylhexoate, cadmium laurate, cadmium stearate, zinc caprylate, cadmium caproate, barium stearate, barium 2-ethylhexoate, barium laurate, barium ricinoleate, lead stearate, aluminum stearate, magnesium stearate, calcium octoate, calcium stearate, cadmium naphthenate, zinc stearate, zinc octoate, cadmium benzoate, cadmium p-tert butyl-benzoate, barium octyl salicylate, cadmium epoxy stearate, strontium epoxy stearate, cadmium salt of epoxidized acids of soybean oil, and lead epoxy stearate. For food grade uses non-toxic stabilizers should be used such as the calcium and zinc salts.

In plastisol formulations there is preferably also included from 0.1 to 10 parts per 100 parts of resin of an epoxy vegetable oil such as epoxidized soybean oil or epoxidized tall oil.

The stabilizers of the present invention are particularly effective as color stabilizers and melt flow stabilizers for olefin polymers such as polyethylene, polypropylene, ethylene propylene copolymers (e. g. 50:50, 80:20 and 20:80), ethylene-monoolefin copolymers wherein the monoolefin has 4-10 carbon atoms and is present in a minor amount, e.g. ethylene-butene-1 copolymer (95:5) and ethylene-decene-1 copolymer (90:10). Furthermore, they can be used to stabilize natural rubber, styrene-butadiene rubber (SBR rubber), e.g. (75% butadiene-25% styrene), EPDM rubbers, ABS terpolymers (e.g. 20-30% acrylonitrile, 20-30% butadiene, 40-60% styrene), polyisoprene, polybutadiene, styrene-acrylonitrile copolymers butyl rubber, polyacrylonitrile and acrylonitrile copolymers (e.g. acrylonitrile-vinyl chloride 85:15), polystyrene, impact modified polystyrene, butadiene acrylonitrile (e.g. 60:40); polymerized acrylates and methacrylate, e.g. polymethyl acrylate polymethyl methacrylates and polybutyl acrylate, polyacetals, e.g. polyoxymethylene polymers (e.g. Delrin and Celcon), polycarbonates (e.g. bisphenol A-carbonate polymer), polysulfones, polyphenyleneoxides, phenoxy resins, epoxy resins, A-epichlor-hydrin, nylon, cellulose acetate, cellulose acetate-propionate, cellulose acetate-butyrate, cellulose nitrate, ethyl cellulose, linear polyesters, e.g. polyethylene terephthalate (Dacron, Mylar), unsaturated polyesters, e.g. vinyl compounds modified alkyds such as ethylene glycol phthalate-maleate modified with styrene or diallyl phthalate, oil modified alkyd resins, e.g. soybean oil-glyceryl phthalate resin, chlorosulfonated polyethylene, polyurethanes (e.g. toluene diisocyanate reaction products with polypropylene glycol molecular weight 2025 or with glycerine-ethylene oxide adduct having a hydroxyl number of 56.

As the EPDM rubber there can be employed many of the commercially available EPDM rubbers. The EPDM rubber normally contains 30 to 70 molar percent (preferably 50 to 60 molar percent) of ethylene, 65 to 20 molar percent (preferably 35 to 45 molar percent) propylene and 1 to 15 molar percent (preferably 3 to 5 molar percent) of the nonconjugated polyolefin. Usually the polyolefin is not over 10 molar percent. The ethylene and propylene can each be 5 to 95 molar percent of the composition.

As used in the present specification and claims, the term nonconjugated polyolefin includes aliphatic nonconjugated polyene hydrocarbons and cycloaliphatic nonconjugated polyene hydrocarbons, e.g. endocyclic dienes. Specific examples of suitable nonconjugated polyolefins include pentadiene-1,4; hexadiene-1,4; dicyclopentadiene, methyl cyclopentadiene dimer, cyclododecatriene, cyclooctadiene-1,5; 5-methylene-2-norbornene.

Specific examples of suitable terpolymers are the Royalenes which contain 55 mole percent ethylene, 40 to 42 mole percent propylene and 3 to 5 mole percent dicyclopentadiene; Enjay terpolymers, e.g. ERP-404 of Enjay and Enjay 3509 which contains about 55 mole percent ethylene, 41 mole percent propylene and 4 mole percent 5-methylene-2-norbornene; Nordel, a terpolymer of 55 mole percent ethylene, 40 mole percent propylene and 5 mole percent hexadiene-1,4. Another suitable terpolymer is the one containing 50 mole percent ethylene, 47 mole percent propylene and 3 mole percent 1,5-cyclooctadiene (Dutrel).

Examples of EPDM rubbers are given in U.S. Pat. Nos. 2,933,480; 3,000,866; 3,063,973; 3,093,620; 3,093,621, and 3,136,739, in British Pat. No. 880,904 and in Belgian Pat. No. 623,698.

There can also be included thio compounds in an amount of 0.01 to 10%, usually 0.1 to 5% of the polymer. Thus, there can be used pentaerythritol tetra (mercaptoacetate), 1,1,1-trimethylolethane tri (mercaptoacetate), 1,1,1-trimethylolpropane tri (mercaptoacetate), dioleyl thiodipropionate, dilauryl thiodipropionate, other thio compounds include distearyl 3,3'-thiodipropionate, dicyclohexyl -3,3'-thiodipropionate, dicetyl-3,3'-thiodipropionate, dioctyl-3,3'-thiodipropionate, dibenzyl-3,3'-thiodipropionate, lauryl myristyl-3,3'-thiodipropionate, diphenyl-3,3'-thiodipropionate, di-p-methoxyphenyl-3,3'-thiodipropionate, didecyl-3,3'-thiodipropionate, dibenzyl-3,3'-thiodipropionate, diethyl-3,3'-thiodipropionate, lauryl ester of 3-methyl-mercapto propionic acid, lauryl ester of 3-butyl-mercapto propionic acid, lauryl ester of 3-lauryl-mercapto propionic acid, phenyl ester of 3-octylmercapto propionic acid, lauryl ester of 3-phenylmercapto propionic acid, lauryl ester of 3-benzylmercapto propionic acid, lauryl ester of 3-(p-methoxy) phenylmercapto propionic acid, lauryl ester of 3-cyclo-hexylmercapto propionic acid, lauryl ester of 3-hydroxy-methylmercaptopropionic acid, myristyl ester of 3-hydroxy-ethylmercapto propionic acid, octyl ester of 3-methoxy-methylmercapto propionic acid, dilauryl ester of 3-carboxyl-methylmercapto propionic acid, dilauryl ester of 3-carboxy-propylmercapto propionic acid, dilauryl-4,7-dithiasebacate, dilauryl -4,7,8,11- tetrathiotetradecandioate, dimyristyl-4,11-dithiatetradecandioate, lauryl-3-benzothiazylmercaptopropionate. Preferably the esterifying alcohol is an alkanol having 10 to 18 carbon atoms. Other esters of beta thiocarboxylic acids set forth in Gribbins U.S. Pat. No. 2,519,744 can also be used.

Likewise, there can be included 0.01 - 10%, usually 0.1 - 5% in the monoolefin polymer formulations. Examples of such salts are calcium stearate, calcium 2-ethylhexoate, calcium octate, calcium oleate, calcium ricinoleate, calcium myristate, calcium palmitate, calcium laurate, barium laurate, barium stearate, magnesium stearate as well as zinc stearate, cadmium laurate, cadmium octoate, cadmium stearate and the other polyvalent metal salts of fatty acids set forth previously.

For food grade uses again calcium and zinc salts are preferred.

There can also be added phenolic antioxidants in an amount of 0.01–10%, preferably 0.1–5%. Examples of such phenols include 2,6-di-t-butyl-p-cresol (Ionol), butylated hydroxyanisole, propyl gallate, 4,4'-thiobis(6-t-butyl-m-cresol), 4,4' cyclohexylidene diphenol, 2,5-di-t-amyl hydroquinone, 4,4'-butylidene bis(6-t-butyl-m-cresol), hydroquinone monobenzyl ether, 2,2'-methylene-bis (4-methyl-6-t-butyl-phenol) (Catalin 14), 2,6-butyl-4-decyloxyphenol, 2-t-butyl-4-dodecyloxyphenol, 2-t-butyl-4-octadecyloxyphenol, 4,4'-methylene-bis (2, 6-di-t-butyl phenol), p-aminophenol, N-lauryloxy-p-aminophenol, 4,4'-thiobis (3-methyl- 6-t-butylphenol), bis [o-1,1,3,3-tetramethylbutyl) phenol] sulfide, 4-acetyl-β-resorcylic acid, A stage p-t-butylphenolformaldehyde resin, crotonaldehyde condensate of 3-methyl-6-t-butyl-phenol, 2, 6-di-t-butyl p-cresol (Toponol CA), 2,2-methylene bis 4-ethyl-6-t-butylphenol (AO-425), 4-dodecyloxy-2-hydroxy-benzophenone, 3-hydroxy-4-(phenylcarbonyl) phenyl palmitate, n-dodecyl ester of 3-hydroxy-4(phenylcarbonyl) phenoxyacetic acid, and t-butylphenol.

The use of epoxy compounds in an amount of 0.01–5% in the polymer compositions is also valuable. Examples of such epoxy compounds include epoxidized soya bean oil, epoxidized lard oil, epoxidized olive oil, epoxidized linseed oil, epoxidized castor oil, epoxidized peanut oil, epoxidized corn oil, epoxidized tung oil, epoxidized cottonseed oil, epichlorhydrinbisphenol A resins (epichlorhydrindiphenylolpropane resins), phenoxy-propylene oxide, butoxypropylene oxide, epoxidized neopentylene oleate, glycidyl epoxystearate, epoxidized α-olefins, epoxidized glycidyl soyate, dicyclopentadiene dioxide, epoxidized butyl tallate, styrene oxide, dipentene dioxide, glyciodol, vinyl cyclohexene dioxide, glycidyl ether of resorcinol, glycidol ether of 1,5-dihydroxynaphthalene, epoxidized linseed oil fatty acids, allyl glycidyl ether, butyl glycidyl ether, cyclohexane oxide, 4-(2,3-epoxypropoxy) acetophenone, mesityl oxide epoxide, 2-ethyl-3-propyl glycidamide, glycidyl ethers of glycerine, pentaerythritol and sorbitol, and 3,4-epoxy-cyclohexane-1, 1-dimethanol bis-9,10-epoxystearate.

Unless otherwise indicated, all parts and percentages are by weight.

EXAMPLE 1

1 mol of pentaerythritol was suspended in 150 cc of phenol and heated to 150° C. There were stripped off 50 grams of phenol at 10 mm. Then there added 2 moles of triphenyl phosphite and 1.5 grams of sodium methylate. The balance of the phenol was stripped out at 15 to 2 mm at 100° to 200° C. There were then added 2.2 moles of stearyl alcohol and stripping was continued at the same temperature in a vacuum to produce a product which consisted of 85–90% distearyl pentaerythritol diphosphite, 5–10% stearyl alcohol and traces of tristearyl phosphite and tripentaerythritol tetraphosphite, F.P. 55°–60° C, as a friable, colorless, odorless solid.

EXAMPLE 2

| Polyvinyl chloride | 100 parts |
|---|---|
| Distearyl pentaerythritol diphosphite | |
| Composition of Example 1 | 0.25 parts |
| Calcium - zinc stearate | 1.0 part |

This composition was useful for making bottles for food uses which had good heat and light stability.

EXAMPLE 3

| Polyvinyl chloride | 100 parts |
|---|---|
| Distearyl pentaerythritol diphosphite | |
| Composition of Example 1 | 0.3 part |
| Calcium stearate | 1.0 parts |

The polyvinyl chloride product prepared had good heat and light stability.

EXAMPLE 4

| Polypropylene | 100 parts |
|---|---|
| Distearyl pentaerythritol diphosphite | |
| Composition of Example 1 | 1.25 parts |
| Calcium stearate | 0.1 part |

EXAMPLE 5

| Polypropylene | 100 parts |
|---|---|
| Distearyl pentaerythritol diphosphite | |
| Composition of Example 1 | 0.5 parts |
| Calcium stearate | 0.1 part |
| 2-hydroxy-4-n-octoxy benzophenone | 0.5 parts |

What is claimed is:

1. A composition comprising distearyl pentaerythritol diphosphite in friable form, said composition consisting essentially of the product prepared by either (1) reacting diphenyl pentaerythritol diphosphite with stearyl alcohol in a molar excess of 10 to 100 molar % or (2) reacting pentaerythritol, triphenyl phosphite and stearyl alcohol, the stearyl alcohol being employed in a molar excess of 10 to 100 molar % of that required to form distearyl pentaerythritol diphosphite.

2. A composition according to claim 1 wherein the composition includes stearyl alcohol and tristearyl phosphite.

3. A composition according to claim 1 in the form of a finely-divided, friable, free-flowing powder.

4. A composition according to claim 1 made by process (1).

5. A composition according to claim 1 made by process (2).

6. A composition according to claim 1 wherein the pentaerythritol and triphenyl phosphite are first reacted together, the phenol formed is stripped off and then the stearyl alcohol is reacted with the product remaining after stripping the phenol.

7. A composition according to claim 6 wherein the materials are employed in the molar ratio of 1 mole pentaerythritol, 2 moles triphenyl phosphite and 2.2 moles stearyl alcohol.

8. A process of preparing a friable distearyl pentaerythritol diphosphite composition comprising either (1) reacting diphenyl pentaerythritol diphosphite with stearyl alcohol in a molar excess of at least 10 molar % or (2) reacting pentaerythritol, triphenyl phosphite and stearyl alcohol, the stearyl alcohol being employed in a molar excess of at least 10 molar % of that required to form distearyl pentaerythritol diphosphite.

9. A process according to claim 8 wherein the process consists essentially of said steps.

10. A process according to claim 8 wherein the molar excess of stearyl alcohol in process (1) is 10 to 100 molar % and in process (2) is 10 to 100 molar %.

11. A process according to claim 8 which is process (1).

12. A process according to claim 8 which is process (2).

13. A process according to claim 12 wherein the pentaerythritol and triphenyl phosphite are first reacted together, the phenol formed is stripped off and then the stearyl alcohol is reacted with the product remaining after stripping the phenol.

14. A process according to claim 13 wherein the materials are employed in the molar ratio of 1 mole pentaerythritol, 2 moles triphenyl phosphite and 2.2 moles stearyl alcohol.

15. A composition of matter comprising a polymer selected from the group consisting of halogen containing polymers and olefin polymers having incorporated therein the composition of claim 1 as a stabilizer therefore.

16. A composition of matter according to claim 15 wherein the polymer is an olefin polymer.

17. The stabilized composition of matter according to claim 16 stabilized against deterioration in the presence of ultraviolet light also including a stabilizing amount of 2-hydroxy-4-n-octoxy benzophenone.

18. The stabilized composition of matter according to claim 17 wherein the olefin polymer is chosen from the group consisting of homopolymers and copolymers of ethylene and propylene.

19. The stabilized composition of claim 18 containing 0.1 to 5% of 2-hydroxy-4-n-octoxy benzophenone and 0.05–1% of the said distearyl pentaerythritol diphosphite composition based on the polymer.

20. The stabilized composition of claim 19 containing 0.5 parts of 2-hydroxy-4-n-octoxy benzophenone and 0.5 parts of said distearyl pentaerythritol diphosphite composition per 100 parts of said polymer.

21. A method for stabilizing an olefin polymer against deterioration in the presence of ultraviolet light comprising the addition of a stabilizing amount of 2-hydroxy-4-n-octoxy benzophenone in combination with a stabilizing amount of the friable distearyl pentaerythritol diphosphite composition of claim 1.

22. The method of claim 21 wherein the 2-hydroxy-4-n-octoxy benzophenone is added in an amount of 0.1 to 5% and the distearyl pentaerythritol diphosphite composition is added in an amount of 0.05–1% based on the polymer.

23. The method of claim 22 wherein there is employed 0.5 parts of 2-hydroxy-4-n-octoxy benzophenone and 0.5 parts of said distearyl pentaerythritol diphosphite composition per 100 parts of said polymer.

* * * * *